US00PP18811P2

(12) United States Plant Patent
Heffron

(10) Patent No.: US PP18,811 P2
(45) Date of Patent: May 13, 2008

(54) **NEW GUINEA *IMPATIENS* PLANT NAMED 'BALCEBREDEP'**

(50) Latin Name: *Impatiens hawkeri*
Varietal Denomination: Balcebredep

(75) Inventor: Leslie Heffron, Hickory, NC (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/605,157

(22) Filed: Nov. 28, 2006

(51) Int. Cl.
*A01H 5/00* (2006.01)

(52) U.S. Cl. ..... Plt./318
(58) Field of Classification Search ..... Plt./318
See application file for complete search history.

(56) References Cited

PUBLICATIONS

Canada Plant Breeders' Rights application No. 06–5305 filed Mar. 9, 2006.

European Plant Breeders' Rights application No. 2006/2337 filed Nov. 16, 2006.

*Primary Examiner*—Anne Marie Grunberg
*Assistant Examiner*—Louanne Krawczewicz Myers
(74) *Attorney, Agent, or Firm*—Audrey Charles

(57) ABSTRACT

A new and distinct cultivar of New Guinea *Impatiens* plant named 'Balcebredep', characterized by its single type dark red-colored flowers, variegated medium green and yellow green-colored foliage, and moderately vigorous, compact, and mounded growth habit.

1 Drawing Sheet

Latin name of genus and species of plant claimed: *Impatiens hawkeri*.
Variety denomination: 'Balcebredep'.

BACKGROUND OF THE INVENTION

The present invention relates to a new and distinct cultivar of New Guinea *Impatiens* plant botanically known as *Impatiens hawkeri* and hereinafter referred to by the cultivar name 'Balcebredep'.

The new cultivar originated in a controlled breeding program in Arroyo Grande, Calif. during November 2003. The objective of the breeding program was the development of New Guinea *Impatiens* cultivars with numerous large flowers, excellent basal branching, and a compact, mounded growth habit.

The new New Guinea *Impatiens* cultivar is the result of cross-pollination. The female (seed) parent of the new cultivar is the proprietary *Impatiens hawkeri* breeding selection designated 7824-3, not patented, characterized by its single type medium red-colored flowers, dark green-colored foliage, and upright growth habit. The male (pollen) parent of the new cultivar is the proprietary *Impatiens hawkeri* breeding selection designated 7830-2, not patented, characterized by its single type dark red-colored flowers, dark green-colored foliage, and upright growth habit. The new cultivar was discovered and selected as a single flowering plant within the progeny of the above stated cross-pollination during April 2004 in a controlled environment at Arroyo Grande, Calif.

Asexual reproduction of the new cultivar by terminal stem cuttings since April 2004 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcebredep' as a new and distinct cultivar of New Guinea *Impatiens* plant:

1. Single type dark red-colored flowers;
2. Variegated medium green and yellow green-colored foliage; and
3. Moderately vigorous, compact, and mounded growth habit.

Plants of the new cultivar differ from plants of the female parent primarily in flower color, foliage color, and growth habit and from plants of the male parent primarily in foliage color and growth habit.

Of the many commercially available New Guinea *Impatiens* cultivars known to the inventor, the most similar in comparison to the new cultivar is Celebrette Red 'Balcebred', U.S. Plant Pat. No. 13,994. However, in side by side comparisons, plants of the new cultivar differ from plants of 'Balcebred' in the following characteristics:

1. Plants of the new cultivar have fewer flowers than plants of 'Balcebred'; and
2. Plants of the new cultivar have a foliage color different from plants of 'Balcebred'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcebredep'. The plants were grown in 4.5 inch pots for 12 weeks in a greenhouse at West Chicago, Ill.

DETAILED BOTANICAL DESCRIPTION

Figure 1:
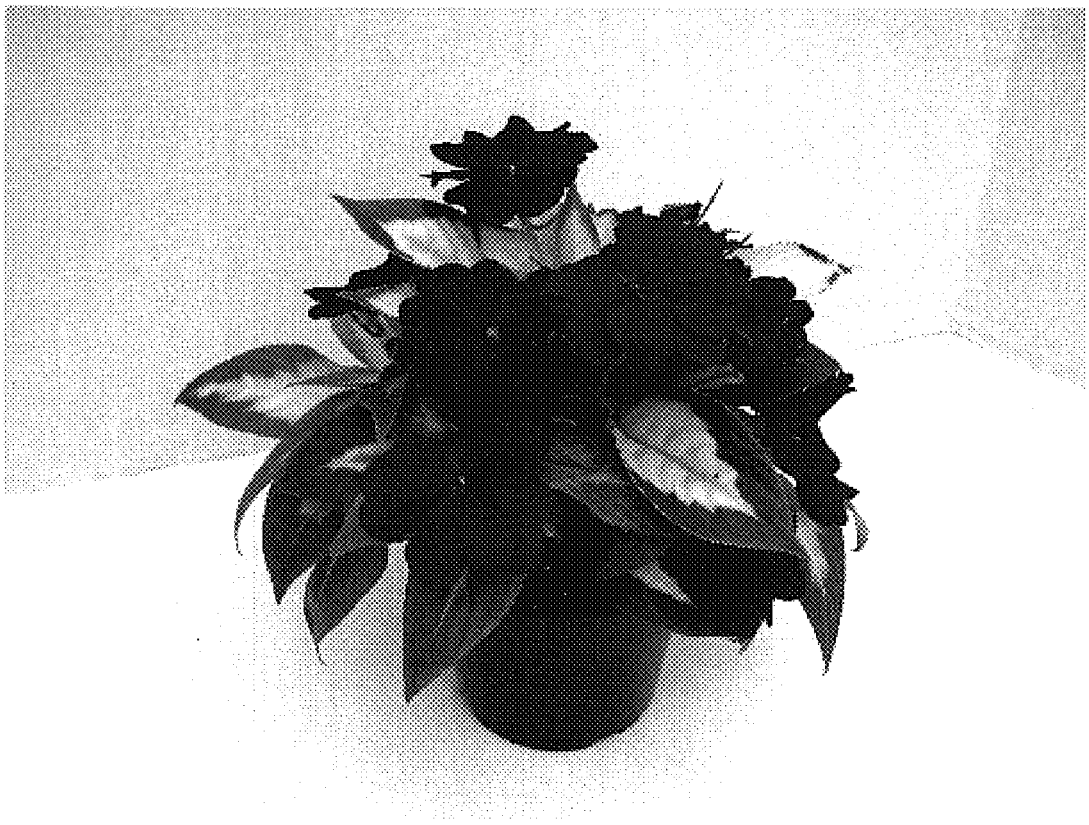
FIG. 1 illustrates a side view of the overall growth and flowering habit of 'Balcebredep'.
Figure 2:
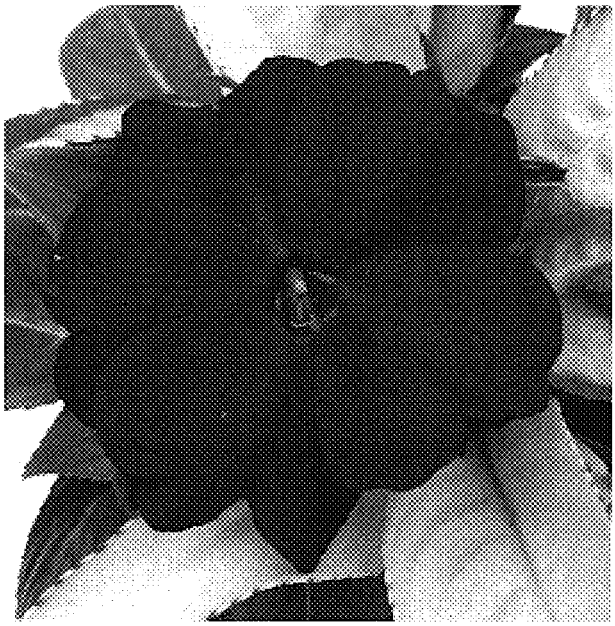
FIG. 2 illustrates a close-up view of an individual flower of 'Balcebredep'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein as The R.H.S. Colour Chart of The Royal Horticultural Society, London, England, 2001 edition, except where general color terms of ordinary significance are used. The color values were determined on Jul. 26, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 12 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens hawkeri* cultivar Balcebredep.

Parentage

*Female parent.*—*Impatiens hawkeri* breeding selection designated 7824-3, not patented.

*Male parent.*—*Impatiens hawkeri* breeding selection designated 7830-2, not patented.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 6 to 8 weeks from a rooted cutting.

*Growth habit and general appearance.*—Moderately vigorous, compact and mounded.

*Size.*—Height from soil level to top of plant plane: Approximately 14.6 cm. Width: Approximately 23.4 cm.

*Branching habit.*—Freely basal branching. Quantity of main lateral branches per plant: Approximately 6.

*Branch.*—Strength: Strong. Length: Approximately 7.7 cm. Diameter: Approximately 5.0 mm. Length of central internode: Approximately 1.9 cm. Texture: Glabrous. Color of young and mature stems: 145C.

Foliage description:

*General description.*—Quantity of leaves per main branch: Approximately 7. Fragrance: None. Form: Simple. Arrangement: In whorls of 3 to 5 leaves.

*Leaves.*—Aspect: Petiole is at acute angle to stem and leaf blade is perpendicular to stem. Shape: Elliptic. Margin: Serrate, ciliate. Apex: Acuminate. Base: Attenuate. Venation pattern: Pinnate. Length of mature leaf at center of stem: Approximately 9.4 cm. Width of mature leaf at center of stem: Approximately 4.5 cm. Texture of upper surface: Sparsely pubescent. Texture of lower surface: Glabrous and sparsely pubescent on midvein. Color of upper surface of young foliage: Variegated, having varying amounts of 137B from margin of apex to upper half of leaf, and remaining portion 154C with venation of 145D. Color of lower surface of young foliage: Variegated, having varying amounts of 138B from margin of apex to upper half of leaf, and remaining portion 154D with venation of 145D. Color of upper surface of mature foliage: Variegated, having margins of 137A, a center of 2D, and venation of 145D with a faint overlay of 186C primarily on the midvein. Color of lower surface of mature foliage: Variegated, having margins of 138B, a center of 2D, and venation of 145D with a faint overlay of 186C on the midvein.

*Petiole.*—Length: Approximately 2.9 cm. Diameter: Approximately 3.6 mm. Texture: Glabrous. Color: 145D.

Flower description:

*Flowering habit.*—'Balcebredep' is freely flowering under outdoor growing conditions with substantially continuous blooming from spring through autumn and year-round in greenhouse environment.

*Lastingness of individual flower on the plant.*—Approximately 5 to 7 days.

Flower description:

*General description.*—Type: Single. Quantity per plant: Approximately 11. Fragrance: None.

*Bud.*—Rate of opening: Generally takes 3 to 4 days for bud to progress from first color to fully open flower. Quantity showing color per plant: Approximately 3.

*Bud just before opening.*—Shape: Ovoid. Length: Approximately 2.0 cm. Diameter: Approximately 1.4 cm. Color: 46A.

*Corolla.*—Shape: Round, cupped when first open with petals turning downward with age. Width: Approximately 6.2 cm. Depth: Approximately 1.2 cm. Borne: Above and below foliage.

*Petals.*—Quantity: 5. Shape (all petals): Obovate. Aspect: Flat. Appearance: Iridescent. Margin: Entire. Apex: Emarginate. Base of upper petal: Truncate. Base of lateral and lower petals: Attenuate. Length of upper petal: Approximately 2.6 cm. Width of upper petal: Approximately 4.5 cm. Length of lateral petals: Approximately 2.9 cm. Width of lateral petals: Approximately 3.0 cm. Length of lower petals: Approximately 3.4 cm. Width of lower petals: Approximately 3.4 cm. Texture of upper and lower surfaces: Glabrous. Color of upper surface when first open: Closest to 46A. Color of lower surface when first open: 47B. Color of upper surface when fully open: Between 46A and 46B. Color of lower surface when fully open: Closest to 47C.

*Spur.*—Quantity: 1 per flower. Length: Approximately 5.3 cm. Diameter at tip: Approximately 1.0 mm. Diameter at base: Approximately 3.0 mm. Texture: Glabrous. Color: 185B and tip of 144C.

*Peduncle.*—Strength: Strong. Aspect: Acute angle to stem. Length: Approximately 4.6 cm. Diameter: Approximately 2.0 mm. Texture: Glabrous. Color: 145D with a faint overlay of 185D.

*Sepals.*—Quantity per flower: 4, with one fused to base of upper petal. Sepal arrangement: 1 spurred lower sepal located between 2 side (lateral) sepals. Shape of lateral and lower sepals: Ovate. Apex of all sepals: Acuminate. Margin of all sepals: Entire. Base of lateral sepals: Broadly attenuate. Base of lower sepal modified into a spur. Length of lateral sepals: Approximately 1.2 cm. Width of lateral sepals: Approximately 7.2 mm. Length of lower sepal: Approximately 1.5 cm. Width of lower sepal: Approximately 1.5 cm. Texture of upper and lower surfaces of all sepals: Glabrous. Color of upper and lower surfaces of lateral sepals: 145D with a faint overlay of 185D and tip of 144B. Color of upper and lower surfaces of lower sepal: N155B with an overlay of 185C and tip of 144B.

*Reproductive organs.*—Androecium: Stamen quantity: 5 per flower, fused around pistil at apex. Anther shape: Hooded. Anther length: Approximately 3.0 mm. Anther color: 160D at apex transitioning to 46C toward filament. Filament color: 155D with an overlay of 46C. Pollen amount: Moderate. Pollen color: 155D. Gynoecium: Pistil quantity: 1 per flower. Pistil length: Approximately 5.0 mm. Stigma shape: 5-pointed star. Stigma color: Colorless, transparent. Style color: 144A. Ovary texture: Glabrous. Ovary color: 144A.

Seed and fruit production: Neither seed not fruit production has been observed.

Disease and pest resistance: Resistance to pathogens and pests common to New Guinea New Guinea *Impatiens* has not been observed.

What is claimed is:

1. A new and distinct cultivar of New Guinea *Impatiens* plant named 'Balcebredep', substantially as herein shown and described.

* * * * *